United States Patent [19]

Downs

[11] Patent Number: 4,773,411
[45] Date of Patent: Sep. 27, 1988

[54] METHOD AND APPARATUS FOR VENTILATORY THERAPY

[76] Inventor: John B. Downs, 8530 Preston Mill Ct., Dublin, Ohio 43017

[21] Appl. No.: 860,821

[22] Filed: May 8, 1986

[51] Int. Cl.$^4$ ............................................ A61M 16/00
[52] U.S. Cl. ............................ 128/204.18; 128/204.21
[58] Field of Search ................... 128/204.18, 204.21, 128/204.25, 204.26, 204.29

[56] References Cited

U.S. PATENT DOCUMENTS

| | | | |
|---|---|---|---|
| 3,358,680 | 12/1967 | Chabanier | 128/142.2 |
| 3,786,809 | 1/1974 | Kitrilakis | 128/205.26 |
| 3,800,793 | 4/1974 | Marrese et al. | 128/188 |
| 3,827,433 | 8/1974 | Shannon | 128/201.23 |
| 3,842,828 | 10/1974 | Bird | 128/204.18 |
| 3,902,487 | 9/1975 | Okmian | 128/204.18 |
| 4,180,066 | 12/1979 | Millken et al. | 128/205.24 |
| 4,182,366 | 1/1980 | Boehringer | 137/510 |
| 4,211,221 | 7/1980 | Schwanbom et al. | 128/204.18 X |
| 4,249,527 | 2/1981 | Ko et al. | 128/204.18 |
| 4,316,458 | 7/1982 | Hammerton-Fraser | 128/205.24 |
| 4,333,452 | 6/1982 | Au | 128/205.24 |
| 4,351,329 | 9/1982 | Ellestad | 128/204.21 |
| 4,466,433 | 8/1984 | Robbins | 128/202.22 |
| 4,502,502 | 3/1985 | Krug | 137/512.3 |
| 4,552,141 | 11/1985 | Torri | 128/205.12 |

OTHER PUBLICATIONS

Downs et al.; "Intermittent Mandatory Ventilation: A New Approach to Weaning Patients from Mech. Ventilators"; Chest, vol. 64, 9-1973, pp. 331-335.
Endre; "A New Type of Breathing Device"; Swedish Lakartidningen; vol. 76, No. 9, 1979, pp. 727-729.
Downs et al.; "Airway Pressure Release Ventilation; A New Concept in Ventilatory Support"; Critical Care Medicine, vol. 15, No. 5, 1987, pp. 459-461.
Stock et al.; "Airway Pressure Release Ventilation"; Critical Care Medicine; vol. 15, No. 5, 1987, pp. 462-466.
Downs et al.; "Intermittent Mandatory Vent.: A New Approach to Weaning Patients from Mech. Ventilators"; Chest 63:525, 9-1973, pp. 1-7.
Desautels et al.; "Methods of Administering Intermittent Mandatory Ventilation"; Respiratory Care, vol. 19, No. 3, 3-1974, pp. 187-191.
Jain et al.; "A Control System for the Long-Term Ventilation of the Lungs"; IEEE Trans. on Biomed Engr., vol. BME-19, No. 1, 1-1972, pp. 47-53.

Primary Examiner—Edward M. Coven
Assistant Examiner—Angela D. Sykes
Attorney, Agent, or Firm—Carothers & Carothers

[57] ABSTRACT

A novel respiratory method and apparatus permits ventilatory therapy in patients requiring respiratory assistance by establishing a substantially continuous positive airway pressure to enhance functional residual capacity, and a periodic release of the substantially continuous positive airway pressure reduces airway pressure at intervals to permit passive reduction in lung volume below functional residual capacity to thereby enhance alveolar ventilation and carbon dioxide excretion.

12 Claims, 2 Drawing Sheets

METHOD AND APPARATUS FOR VENTILATORY THERAPY

BACKGROUND OF THE INVENTION

It is well known and accepted medical practice to treat patients afflicted with respiratory disorders by use of mechanical ventilatory therapy. Treatment of patients with acute lung injury and/or respiratory failure often is complicated by any number of physiologic derangements imposed by the disease process or the physical injury, and morbidity and mortality can be quite high for such patients. A consensus has developed in the medical community that mechanical ventilatory techniques produce detrimental side effects, and that the observed morbidity and mortality often are secondary to the complications produced by the conventional modes of mechanical ventilatory therapy.

Patients who require total mechanical ventilatory support rarely will tolerate continuous positive airway pressure (CPAP) levels in excess of 20 CM $H_2O$ because conventional assisted respiration, in combination with CPAP therapy, results in continual application of elevated mean and peak airway pressures at which lung capacity exceeds normal functional residual capacity (FRC). This sort of mechanical ventilation therapy also may lead to detrimental cardiovascular effects such as negation of the natural augmentation of venous return that attends spontaneous respiration, and in decreased cardiovascular output.

Such patients also commonly exhibit markedly decreased lung compliance which results in extremely high airway pressures during mechanical inspiration thereby greatly increasing the risk of barotrauma (for example, subcutaneous emphysema, pneumothorax and pneumopericardium). Renal, hepatic, and cerebral function may also be impaired in patients who are ventilated with high peak and mean airway pressures.

Patients with acute respiratory failure also commonly exhibit, in addition to decreased lung volume and decreased lung compliance, mismatching of ventilation and perfusion causing arterial hypoxemia, tachypnea and increased work of breathing. This clinical presentation leads to the impression that these patients require external ventilatory assistance, usually with positive pressure mechanical ventilation.

Among the conventional mechanical ventilation techniques are assist mechanisms, intermittent mandatory ventilation (IMV), positive end-expiratory pressure (PEEP), and high frequency low-tidal volume therapy such as applied in infant ventilation. These have been proposed to improve ventilatory therapy and to thereby decrease the rate and severity of complications. Yet in spite of these attempts, the mortality rate from respiratory failure has changed little in many years.

Among the prior art patents known to applicant pertaining to ventilatory techniques and apparatus are the following: U.S. Pat. Nos. 4,552,141; 4,502,502; 4,466,433; 4,351,329; 4,333,452; 4,316,458; 4,182,366; 4,180,066; 3,800,793 and 3,358,680.

BRIEF SUMMARY OF THE INVENTION

As mentioned above, one shortcoming of prior ventilatory techniques generally is that they impose excessively elevated peak and mean airway pressures on the patient. Therapies designed to increase impaired FRC and lung compliance, and to thereby decrease (i.e., optimize) the work of breathing, are physiologically more sound, but the conventional respiratory therapies, with the exception of CPAP, do not attain these objectives. CPAP has been shown to attain these objectives and has been claimed by some to decrease the rates of morbidity and mortality associated with other conventional ventilatory techniques; however, as noted above CPAP along is not sufficient ventilatory assistance for all patients.

Those patients who, under CPAP therapy, cannot achieve adequate alveolar ventilation will experience excessive work of breathing, and in general those patients have been treated with positive pressure ventilation techniques, usually either with assist-control ventilation or intermittent mandatory ventilation (IMV), in an effort to augment alveolar ventilation and carbon dioxide excretion.

The present invention, referred to as airway pressure release ventilation, or APRV, offers a novel and improved method and apparatus for augmentation of alveolor ventilation and $CO_2$ excretion in patients who require CPAP. To understand the invention, it is useful to view breathing (i.e. inspiration and expiration) as the primary mechanism for $CO_2$ excretion and maintenance of adequate FRC as the primary mechanism of oxygenation. That is, the FRC air contains a high concentration of $CO_2$, which is removed from the lungs by repeated inhalation of ambient air, mixing of the inhaled air with the FRC air, and subsequent exhalation which carries away a proportionate quantity of the $CO_2$. Oxygenation is achieved by the absorption of oxygen from the air in the lungs through the alveolar wall on a continuous basis. Thus, the mechanical mixing of oxygen from inhaled air into the FRC air, and of $CO_2$ from the FRC air into the inhaled air, directly impacts the efficiency of $CO_2$ excretion and oxygenation. If FRC is decreased, a tendency may develop for oxygen availability at the alveolar wall to lag behind oxygen demand. Similarly, with impaired FRC and lung compliance, reduced tidal volume, secondary to increased work of breathing, results in reduced efficiency of $CO_2$ excretion and therefore a tendency for the $CO_2$ concentration in the FRC air to increase as the time rate of $CO_2$ elimination is directly related to tidal volume, or more precisely to the time rate (liters per minute) of ambient air exchange. Thus, in patients with impaired FRC and/or lung compliance, the spontaneous respiration rate may increase above normal rates to compensate for impaired efficiency of $CO_2$ excretion and/or oxygenation. Although CPAP is useful in ventilatory therapy under such conditions, CPAP plus conventional mediated breathing techniques may not be since the imposed mean and peak airway pressures are significantly above the CPAP pressure, which is the pressure that restores normal FRC.

This invention avoids the above and other shortcomings of prior mechanical ventilatory techniques and provides improved ventilation therapy by avoiding excessively high mean and peak airway pressures. Instead of superimposing cycles of elevated airway pressure upon a CPAP base pressure level, APRV achieves augmentation of alveolar ventilation and $CO_2$ excretion through intermittent cycles of reduced airway pressure below the CPAP pressure level. Thus, in APRV the level of applied CPAP is selected to improve lung mechanics and gas exchange, and cycles of reduced airway pressure are simultaneously applied at a suitably rate or frequency to insure an appropriate rate of alveolar ventilation and to enhance $CO_2$ excretion. With this technique, mean airway pressure will be slightly lower than the CPAP level and peak airway pressure will not exceed the CPAP level. Spontaneous ventilation can continue in an unrestricted manner between the mechanically mediated breaths. By limiting airway pressure in this fashion, barotrauma and adverse effects on cardiac output would be expected to occur less frequently than with conventional mechanical ventilation techniques.

It is therefore one object of this invention to provide a novel and improved method and apparatus for mechanically assisted ventilation of patients.

A more specific object of the invention is to provide a method and apparatus for improved modes of assisted ventilation wherein alveolar ventilation and $CO_2$ excretion are enhanced without external application of airway pressure above the elevated pressure which provides the patient with near normal or selected optimal FRC.

Another object of the invention is to provide a course of ventilation therapy wherein mediated breaths are induced by reduction of airway pressure below an otherwise continuously maintained positive airway pressure.

Still another object of the invention is to provide a course of ventilation therapy as above specified wherein the continously maintained positive airway pressure is a pressure level above ambient atmospheric which restores normal or near normal FRC, or alternatively establishes an optimal, empirically determined FRC, and which additionally enhances lung compliance in patients having impaired FRC and lung compliance.

BRIEF DESCRIPTION OF THE DRAWINGS

These and other objects and further advantages of the invention will be more readily appreciated upon consideration of the following detailed description and the accompanying figures, in which.

DESCRIPTION OF THE PREFERRED EMBODIMENTS

Figure 1:
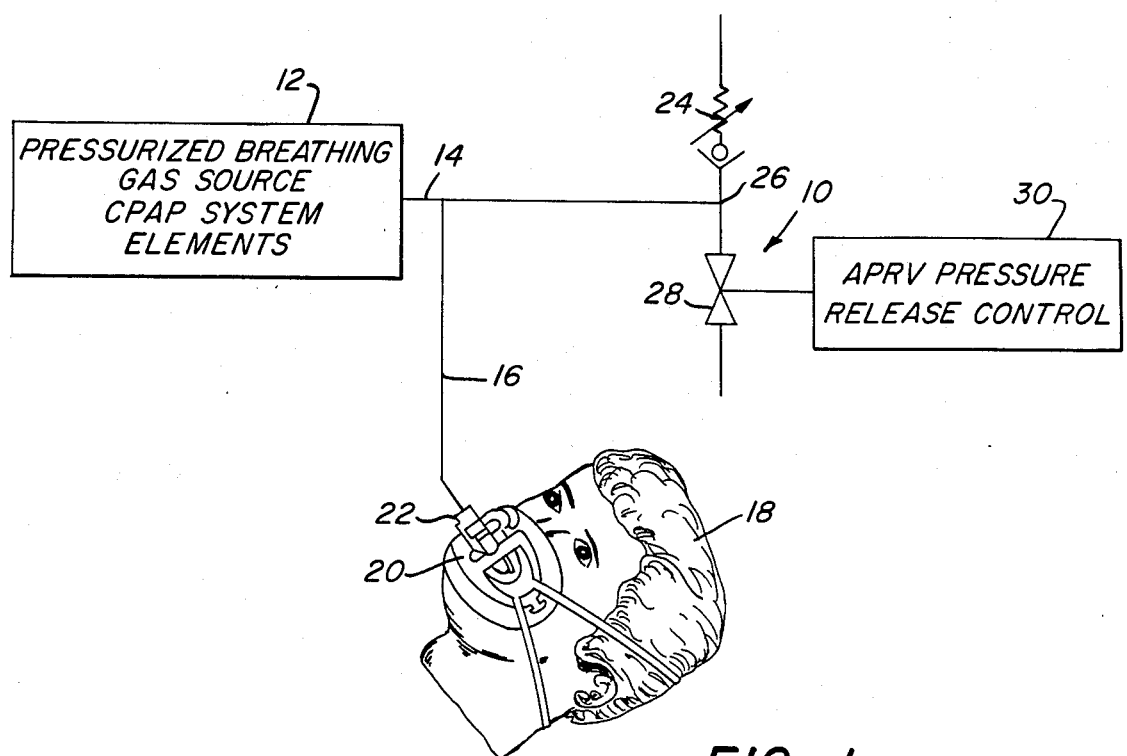
FIG. 1 is a simplified schematic illustration of a ventilation apparatus of the present invention.

There is generally indicated at 10 in FIG. 1, in simplified schematic form, a ventilation system according to the present invention and comprising a ventilator apparatus 12 which provides a source of pressurized breathing gas and other CPAP system control elements, and having connected thereto a gas delivery conduit 14 for delivery of a suitable breathing gas mixture via conduit branch 16 to a patient 18. The breathing gas mixture may be supplied to the patient 18 via any suitable appliance, for example a tight fitting tracheal tube or a tracheal tube with a cuff that forms a tracheal seal in the airway of the patient. Another option is a tight fitting mask applied to the patient's face. These or other conventional breathing gas supply appliances may be utilized. The appliance shown in FIG. 1 is an endotracheal tube holder 20 that is strapped to the face of patient 18 to retain and support an endotracheal tube 22 within the airway of patient 18 in the conventional manner. Also forming a part of ventilation apparatus 10 as an element of CPAP pressure control is an adjustable pressure relief valve 24 which is connected to conduit 14 at junction 26 and which operates to establish the CPAP pressure level by opening in response to pressure excursions exceeding the selected CPAP level. Such pressure excursions occur during spontaneous patient expiration. Typically, valve 24 may be a mushroom type valve which is controlled by a control pressure from the ventilator 12. Alternatively, valve 24 may be any valve with low flow resistance which is programmed to open and close at a predetermined pressure. An exhaust valve 28 is also connected to conduit 14 at junction 26 to open conduit 14 to the ambient atmosphere upon actuation thereof by an APRV pressure release control 30. If desired valve 28 may release pressure to some level above ambient, but lower than the CPAP pressure level. Also, valve 28 may release expiratory gas into a spirometer or other device or container but the pressure must still be lower than CPAP.

Of course, the cross-sectional flow areas and gas flow path lengths of conduits 14, and 16, and of valves 24 and 28, are such that in the overall system design the desired control of pressure levels, as below described, may be readily established through suitable programming and-/or adjustment of the ventilator 12, control unit 30, and valves 24 and 28.

The apparatus 10 is operable to provide patient 18 with APRV as follows. A continuous supply of breathing gas is provided from ventilator system 12 via the conduits 14 and 16 to patient 18. The gas pressure fills the conduits of apparatus 10 and therefore also reaches valves 24 and 28. Valve 24 is set to a preselected CPAP pressure level to preclude CPAP pressure excursions. The elements of the CPAP system, namely ventilator 12 and connected valve 24, are well known in the art and further detailed description thereof is believed to be unnecessary for an understanding of the present invention. It will suffice to note that the CPAP system elements function in the conventional manner to maintain a selected level of CPAP (continuous positive airway pressure) that restores normal or establishes optimal patient FRC (thus maintaining increased lung volume) and enhances lung compliance while permitting spontaneous inspiration and expiration by the patient at a substantially constant elevated airway pressure. At selected intervals, valve 28 is opened to permit system pressure (and therefore, patient airway pressure) to drop a controlled increment, and for a selected interval of time, below the CPAP pressure level. The pressure drop may go fully to ambient pressure or may reach a threshhold level between CPAP and ambient pressure. The frequency of these pressure drops, as well as the rate, magnitude and duration of pressure drop, are controlled to provide periodic cycles of assisted exhalation for improved $CO_2$ excretion and other benefits without resorting to airway pressure excursions above FRC. The mechanics, apparatus and method of the invention are described in more detail hereinbelow; however, for an initial better understanding of the invention, it is helpful to consider a comparison between the physiological effects attained thereby and the effects of conventional ventilatory techniques as shown in FIGS. 2 and 3.

Figure 2:
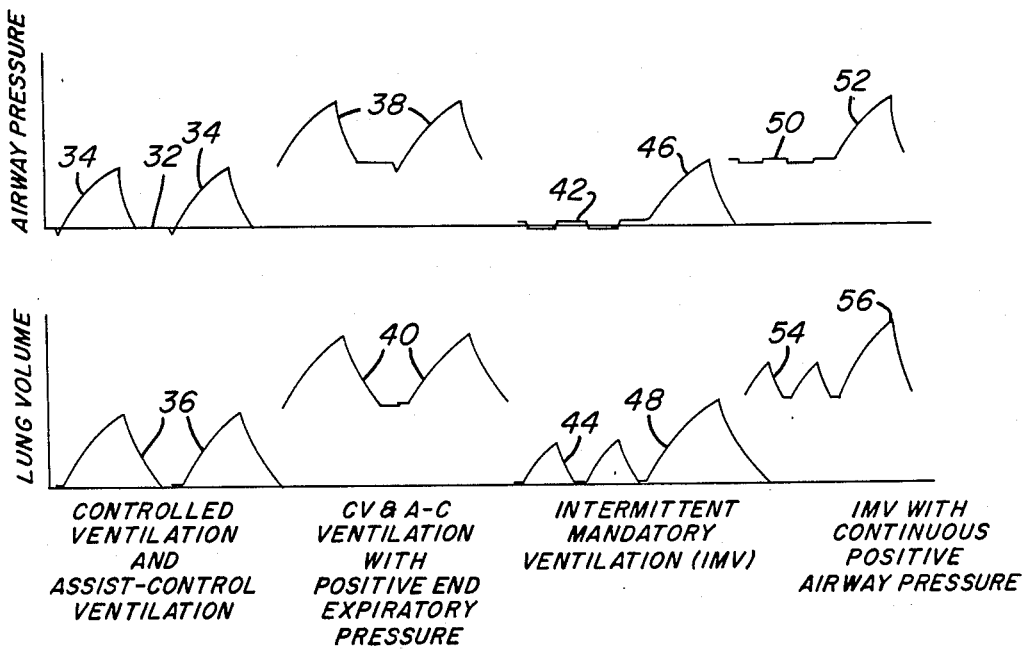
FIGS. 2 and 3 illustrate simultaneously generated traces of lung volume versus time and airway pressure versus time for prior ventilatory therapies.
Figure 3:
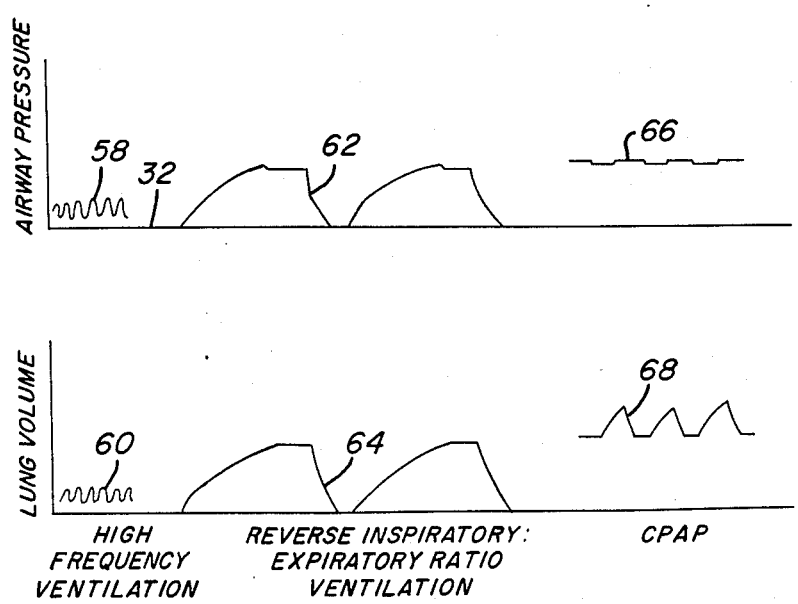

Referring first to FIG. 2, conventional positive pressure ventilation generally is provided by imposing a transient increase in patient airway pressure over a base pressure to induce inspiration, thus causing inspired gas to enter the lungs. During the expiratory phase of the ventilation cycle the airway pressure is returned to the base pressure. The base pressure in all conventional ventilatory therapies corresponds to the patient's FRC. Under assist-control (A-C) ventilation the inspiration phase is triggered by a patient induced drop in airway pressure, whereas under controlled ventilation (CV) the start of inspiration is time-cycled. In either case, patient airway pressure rises from ambient pressure (the base pressure) 32 to a maximum, thus providing assisted inspiration, and subsequently airway pressure returns to ambient to provide assisted expiration and thereby complete a respiration cycle as shown by airway pressure traces 34. During the CV and A-C ventilation cycles, lung volume follows the traces depicted at 36 as lung volume is directly proportional to airway pressure. Positive pressure application may be controlled by pressue (pressure-limited) or pressure cycled ventilation, volume (volume limited or volume cycled ventilation), time (time cycled or controlled ventilation), or flow (flow limited, pressure assisted ventilation). The expiratory phase may be controlled by either time or pressure. If, in the above modes of ventilation, the expiratory phase of each cycle is augmented by including an increase in expiratory airway pressure (i.e. positive end-expiratory pressure or PEEP), the pressure and volume traces would be elevated as indicated in FIG. 2 at 38 and 40.

Some ventilation techniques, referred to as intermittent mandatory ventilation or IMV, will allow a patient to breathe spontaneously between mechanically induced positive pressure breaths. The resulting pressure and volume traces show spontaneous ventilation at 42 and 44, respectively, in FIG. 2, with a cycle of mechanically induced respiration shown at 46 and 48. If such ventilatory technique is combined with CPAP, the spontaneous and induced portions of the airway pressure trace would appear as at 50 and 52, respectively, whereas the spontaneous and induced portions of the lung volume trace would appear as at 54 and 56. Referring now to FIG. 3, other conventional ventilatory techniques include high frequency, low-tidal volume systems (e.g. infant ventilators) which produce above-ambient airway pressure and lung volume traces as at 58 and 60. Pressure and volume traces for other conventional modes of assisted ventilation include reverse inspiratory-expiratory ratio ventilation (62,64) and CPAP (66,68).

Figure 4:
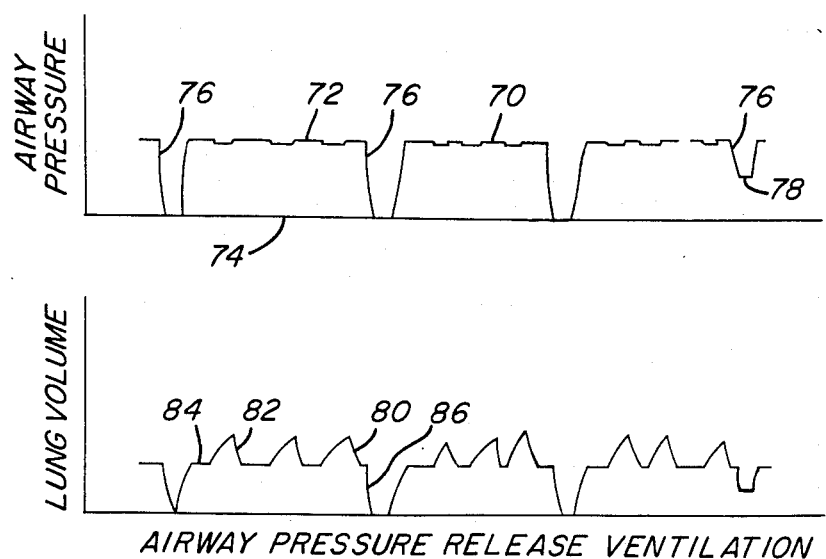
FIG. 4 illustrates simultaneously generated traces of lung volume and airway pressure versus time for the novel technique of airway pressure relief ventilation.

By contrast to the above, FIG. 4 illustrates simultaneously generated traces of airway pressure and lung volume for a patient under APRV ventilatory therapy. A pressure trace 70 illustrates CPAP pressure component 72 maintained at a selected base level above ambient pressure 74 to provide optimal FRC and enhanced lung mechanics. At predetermined intervals, airway pressure is released (by opening of valve 28) to provide as rapid as possible an airway pressure decrease as shown at 76. The pressure decrease may proceed fully to ambient pressure or may be truncated by a positive pressure limit or threshhold as shown at 78.

The patient being treated with APRV will undergo lung volume variation as indicated by trace 80, with spontaneous breathing producing cyclic volume increases and decreases 82 above the CPAP imposed FRC volume 84, and the pressure release below CPAP pressure producing periodic decreases from, and subsequent return to the imposed FRC volume 84 as shown at 86.

The present invention, as described, permits augmentation of alveolar ventilation as an adjunct to CPAP therapy by periodic reduction of airway pressure below the CPAP level. During APRV, CPAP may be applied to a pressure level determined to be desirable, based on a variety of physiologic measurements, calculations and observations. These may include, inter alia, observation of respiratory effort, respiratory rate, depth of respiration, arterial oxygen tension, calculated right-to-left intra-pulmonary shunting of blood and lung-thorax compliance. If it is determined that mechanically assisted ventilation is desirable, rather than applying intermittent increases in airway pressure above the pressure of optimal FRC, followed by airway pressure reduction to the FRC level, APRV is initiated by allowing cyclical release of the CPAP to a lower airway pressure no less than ambient atmospheric pressure. Thus, the assisted ventilation occurs at pressure and volume levels which are less than, as opposed to greater than, the CPAP pressure and the optimal FRC, respectively. This assisted exhalation enchances $CO_2$ excretion by causing an airway pressure reduction 78 and corresponding lung volume reduction 86 below FRC. As a result, $CO_2$ laden gas leaves the lungs. The degree of ventilatory assistance provided by APRV will be determined by the frequency and duration of pressure release 76, the level of CPAP, the pressure release level, the patient's lung-thorax compliance and the flow resistance of the airway pressure release valve 28.

As opposed to conventional mechanical ventilation, APRV will allow spontaneous inhalation to occur whenever the patient attempts to breathe. Exhalation will occur passively following any normal spontaneous breath and additionally at predetermined intervals when airway pressure is released. Accordingly, the enhancement of $CO_2$ excretion and alveolar ventilation occurring during airway pressure release is achieved independent of patient effort. Although subsequent reinstitution of positive pressure following a pressure release may appear at first glance to be similar to conventional mechanical inspiration, there are considerable significant differences which may be illustrated by analysis of the above-described pressure and volume tracings. During APRV, the base line lung volume, or FRC is determined by the imposed CPAP level. During spontaneous inspiration 72, lung volume increases above FRC and during spontaneous exhalation it decreases, returning to the imposed FRC level 84. The entire cycle occurs with little alteration in airway pressure. During airway pressure release 76, lung volume decreases (86), and following reapplication of CPAP, increases back to FRC 84. With all forms of conventional mechanical ventilation, lung volume is increased above FRC, whether it be normal or artificially maintained FRC, during inspiration. This holds true for both mechanically induced and spontaneous breaths. Lung volume subsequently decreases to FRC during exhalation. Thus, no prior mode of mechanical ventilation augments alveolar ventilation and causes excretion of $CO_2$ by decreasing lung volume below FRC. This is a crucial difference because FRC is not merely an arbitrary lung volume parameter, it is the lung volume which minimizes work of breathing, and oxygen at ion efficiency as explained above.

To recapitulate briefly, a combination of pressurized gas containing elements are provided to the airway pressure release circuit 10 to maintain a nearly constant continuous positive airway pressure such that spontaneous breathing causes neither significant increase nor decrease in airway pressure. The positive pressure gas maintains an increased FRC over the FRC volume which would result during breathing of gas at atmospheric pressure. Preferably this is an optimal (i.e. minimal work of breathing) FRC. This increase in FRC is responsible for previously reported benefits of PEEP and CPAP. To accompany the CPAP breathing assistance, positive airway pressure is briefly released at predetermined intervals to allow a transient decrease of airway pressure (and therefore of lung volume) to promote excretion of carbon dioxide from the lungs. The pressure release is of sufficiently limited duration that FRC is re-established before any detrimental effect from loss of FRC may occur.

The disclosed unique ventilation therapy realizes all the beneficial effects of conventional mechanical ventilation without the disadvantages of conventional mechanical ventilators, conventional mechanical ventilator circuits, and conventional CPAP systems and circuits.

As will be be appreciated from the foregoing description, conventional mechanical ventilation techniques function with a control philosophy nearly the opposite of the APRV control philosophy, in that conventional techniques cause active lung expansion to a volume above desired FRC and passive exhalation to FRC. By contrast, ARPV causes an increase in FRC, but assists ventilation by means of airway pressure release thus allowing intermittent passive decrease in lung volume below FRC.

Of course the invention may be practiced in many ways, using a variety of valve configurations. For example, valves 24 and 28 may be combined in a single valve structure having the functional qualities specified above. Ventilator 12 may provide a continuous or intermittent flow of pressurized gas to produce the desired constant increase in airway pressure. Furthermore, it will be understood that system 10 typically will include many features to fulfill other requirements of conventional ventilation systems. For example, the system typically would include variable breathing gas mix, humidification capability, low flow resistance circuitry, and disconnect, APNEA, $O_2$ rate, and temperature alarms, in addition to the illustrated APRV pressure release control element.

These and other features of the invention, as well as various alternative and modified embodiments thereof, would readily occur to those skilled in the art once apprised of may invention. Accordingly, it is intended that the invention be construed as broadly as permitted by the scope of the claims appended hereto.

I claim:

1. A method of providing ventilatory assistance to patients afflicted with impaired spontaneous respiration capability comprising the steps of:
   providing a continuous supply of breathing gas to the airway of such a patient;
   coincident with said providing step, maintaining the airway pressure of such a patient substantially constantly at an elevated base pressure level above ambient atmosphere pressure in a manner to permit substantially continuous spontaneous respiration while the patient's airway pressure is maintained at said elevated base pressure;
   intermittently reducing the airway pressure of such a patient from said elevated base pressure level to a threshold pressure level not substantially less than ambient atmospheric pressure;
   maintaining the airway pressure of such a patient substantially at said threshold pressure level for a time period of predetermined duration; and
   returning the airway pressure of such patient to said elevated base pressure level.

2. The method as claimed in claim 1 wherein said elevated base pressure level is of a magnitude to provide optimal functional residual capacity in the lungs of such a patient.

3. The method as claimed in claim 2 wherein said intermittently reducing step comprises rapid pressure reduction from said elevated base pressure level to said threshold pressure level.

4. The method as claimed in claim 3 wherein said rapid pressure reduction occurs at a rate substantially equivalent to the rate of pressure reduction achieved upon open venting of said elevated base pressure level to the ambient atmosphere.

5. The method as claimed in claim 1 including the additional step of repeating said intermittent reducing, maintaining and returning steps in a continuous repetitive sequence at predetermined intervals.

6. The method as claimed in claim 5 wherein said elevated base pressure level is maintained continuously during the predetermined intervals between the end of each said returning step and initiation of the subsequent intermittently reducing step.

7. The method as claimed in claim 6 wherein the length of said predetermined interval between the end of each said returning step and initiation of the subsequent intermittently reducing step is sufficient to permit at least a plurality of spontaneous breaths by such a patient.

8. In a method of providing external ventilatory assistance to a patient afflicted with impaired spontaneous respiration capability which includes substantially continuous spontaneous patient inspiration and expiration while the patient's airway pressure is substantially constantly maintained at a pressure level greater than ambient atmospheric pressure, the improvement comprising;
   stimulating the alveolar ventilation and carbon dioxide excretion functions of the patient's respiratory system by intermittently reducing said elevated airway pressure to a pressure level not subtantially less than ambient atmospheric pressure for a period of predetermined duration.

9. In an apparatus for providing ventilatory assistance to patients afflicted with impaired spontaneous respiration capability, the combination comprising:
   interfacing means adapted for sealed engagement with the airway of such a patient for delivery of a breathing gas to such patient;
   a breathing gas supply means cooperable with said interfacing means for delivery of breathing gas to the airway of such a patient;
   pressure control means cooperable with said interfacing means to maintain a substantially constant elevated pressure level above ambient atmospheric pressure within the airway of such a patient;
   pressure release means cooperable with said interfacing means to permit controlled momentary release of said elevated pressure level from the airway of such a patient; and
   control means cooperable with said pressure release means to provide repetitive intermittent cycles of momentary airway pressure reduction from said elevated pressure level to a reduced airway pressure level, and return of such patient's airway pressure from said reduced pressure to said substantially constant elevated pressure level.

10. The apparatus as claimed in claim 9 wherein said said pressure control means includes a pressure relief valve for relieving pressure excursions above said substantially constant elevated pressure level.

11. The apparatus as claimed in claim 10 wherein said pressure release means includes a pressure release valve communicating in fluid flow relationship with the airway of such a patient and operable by said control means to open the airway of such a patient to the ambient atmosphere.

12. In an apparatus for providing a substantially constant elevated airway pressure level above ambient atmospheric pressure to the airway of a patient to maintain a selected functional residual capacity within the lungs of such patient, the improvement comprising:

pressure release means repetitively operable to momentarily reduce the airway pressure of such a patient from said substantially constant elevated pressure level to a reduced airway pressure level no less than ambient atmospheric pressure and to subsequently permit return of such patient's airway pressure to said substantially constant elevated pressure level to thereby define an intermittently repeated interval of predetermined limited duration during which such patient's airway pressure is maintained at a reduced pressure level less than said substantially constant elevated pressure level.

* * * * *